United States Patent
Wolski (10) Patent No.: US 8,339,261 B1
(45) Date of Patent: Dec. 25, 2012

(54) SYSTEM AND METHOD OF MONITORING THE DOOR OF A SECURE CABINET FOR HOLDING PHARMACEUTICAL PRODUCTS

(75) Inventor: Keith T. Wolski, Phoenix, AZ (US)

(73) Assignee: Knox Associates, Phoenix, AZ (US)

( * ) Notice: Subject to any disclaimer, the term of this patent is extended or adjusted under 35 U.S.C. 154(b) by 596 days.

(21) Appl. No.: 12/496,575

(22) Filed: Jul. 1, 2009

Related U.S. Application Data (60) Provisional application No. 61/077,430, filed on Jul. 1, 2008.

(51) Int. Cl.
*G08B 21/00* (2006.01)

(52) U.S. Cl. .................. 340/545.6; 340/568.1; 700/231; 70/278.1

(58) Field of Classification Search ............ 340/539.12, 340/545.6, 573.1, 586.1, 5.2, 5.3–5.32; 700/231, 700/242, 244; 70/266, 267, 278.1
See application file for complete search history.

(56) References Cited

U.S. PATENT DOCUMENTS

| | | | |
|---|---|---|---|
| 3,988,909 A | 11/1976 | Catapano | |
| 4,278,968 A | 7/1981 | Arnett et al. | |
| 4,528,558 A | 7/1985 | Steers et al. | |
| 4,583,082 A | 4/1986 | Naylor | |
| 4,663,621 A | 5/1987 | Field et al. | |
| 4,686,912 A | 8/1987 | Fogleman et al. | |
| 4,771,269 A | 9/1988 | Pasty et al. | |
| 4,812,810 A | 3/1989 | Query et al. | |
| RE33,960 E | 6/1992 | Neuman | |
| 5,321,963 A | 6/1994 | Goldman | |
| 6,084,511 A | 7/2000 | Kil | |
| 7,057,510 B2 | 6/2006 | Maniaci | |
| 7,081,816 B2 | 7/2006 | Schebel et al. | |
| 7,242,296 B2 | 7/2007 | Wang et al. | |
| 7,262,698 B1 | 8/2007 | Frederick et al. | |
| 7,394,369 B2 | 7/2008 | Horngren | |
| 2007/0194916 A1 | 8/2007 | Hewitt et al. | |

*Primary Examiner* — Jeffery Hofsass
(74) *Attorney, Agent, or Firm* — Knobbe, Martens, Olson & Bear, LLP (57) ABSTRACT

In one embodiment, a pharmaceutical cabinet comprises sensors positioned within the frame and door of the cabinet, and the sensors are arranged in a predetermined orientation when the door is closed and a lock is actuated. The sensors are configured to communicate with one another when brought into the predetermined orientation to confirm that the door is closed and the lock is actuated. One or both of the sensors may transmit an identifier to the other sensor, and the communication between the sensors may be encoded. The cabinet also includes a sensor on the lock that indicates if the lock is engaged. The cabinet may generate a record of the times the sensors are moved into or out of communication and the times that the lock is engaged.

18 Claims, 6 Drawing Sheets

SYSTEM AND METHOD OF MONITORING THE DOOR OF A SECURE CABINET FOR HOLDING PHARMACEUTICAL PRODUCTS

CROSS-REFERENCE TO RELATED APPLICATIONS

This application is a non-provisional of U.S. Patent Application No. 61/077,430 filed Jul. 1, 2008, entitled "ELECTRONIC PROXIMITY SENSOR" which is fully incorporated herein by reference.

BACKGROUND OF THE INVENTION

1. Field of the Invention

The present invention relates to electronic locking mechanisms and, in particular, concerns an electronic proximity sensor used to validate locking mechanisms and a tracking system used to determine the times the lock was engaged or disengaged and the times that a door was opened or closed.

2. Description of the Related Art

Boxes and cabinets used in emergency vehicles contain drugs, and these boxes and cabinets have mechanical locking mechanisms in place that are intended to prevent people from accessing those drugs. However, it is easy to pretend to close the lock on these boxes and cabinets while having the door still open, for example by flipping the bayonet of the locking device over to allow the box and/or cabinet to appear locked when it is not.

In the normal construction of a locked box or cabinet, the assumption is that when the lock is engaged the box or cabinet is actually locked. However, mechanical gears can be easily manipulated to fool the box or cabinet to think the bolt is engaged while the door is open. Thus, any sensors that are based on the position of mechanical locking mechanisms can also be fooled. In other words, when using only mechanical locking mechanisms, it is possible to have the bolt extended but for the box or cabinet to not be really locked. For applications where the contents of the box or cabinet need to be absolutely secured, mechanical locking gears are not sufficient.

However, many secure boxes and cabinets comprise metal, and proximity sensors that communicate electromagnetically, such as through induction, do not operate well or at all with a box or cabinet that comprises metal since the metal absorbs the electromagnetic energy. Furthermore, a proximity sensor that detects metal can be easily fooled by positioning metal nearby. Thus, there is a need for a locking validation mechanism that can confirm that the mechanical locking is indeed effective, such as by verifying that a door is closed and that a lock is engaged, and that can operate in an environment where it is substantially surrounded by metal.

Also, medical personnel must access the drugs contained in a box or cabinet during the course of duty to administer the drugs to a patient in need. Therefore, these medical personnel must have the ability to unlock the box or cabinet. However, once these medical personnel have the ability to access the drugs they may remove more of the drugs than is necessary for legitimate treatment of patients. For example, when responding to an emergency call an emergency medical technician may engage in an authorized access of the drugs in the box or cabinet but may remove more drugs than are needed to treat a victim and later engage in unauthorized use of the extra drugs. Or a health care employee with access to the cabinet may unlock the cabinet when no other people are nearby and remove some of the drugs for unauthorized purposes.

Therefore there is a need for a device that facilitates the auditing of any access made to the contents of a box or cabinet. Such a device would advantageously help determine who unlocked/opened the box or cabinet. Consequently, the device would help reduce unauthorized use of the contents of the box or cabinet, which would further reduce the costs of the supplier of the contents, for example by reducing the costs of stocking the box or cabinet with pharmaceuticals. The device would also help reduce the risk of injury to users who may be engaging in unauthorized use of the contents by impairing the access of such users to the contents.

SUMMARY OF THE INVENTION

The aforementioned need is satisfied by the electronic proximity sensor of the present invention which, in one particular aspect, is triggered only when the door and frame of a box or cabinet are within a predefined distance from one another and the lock indicates that is it actuated, thereby confirming that the lock is actually engaged and the door is closed. In this implementation, the predefined distance must be small enough to confirm that the box or cabinet is indeed closed and the lock engaged. Furthermore, the electronic proximity sensor must operate in a metal environment.

In one embodiment, a storage container for medical pharmaceuticals comprises a frame that defines a partially enclosed space that is configured to receive medical pharmaceuticals, wherein the frame defines an opening, a door mounted to the frame so as to be movable between an open position, whereby access to the medical pharmaceuticals can be obtained, and a closed position whereby the medical pharmaceuticals can be secured within the partially enclosed space, a locking mechanism that locks the door to the frame in the closed position, and a lock verification system. The lock verification system includes a first component mounted on the door and a second component mounted on the frame, wherein the first component and the second component are communicatively coupled so that when the first component and the second component are positioned in a first orientation relative to each other with the door in the closed position, a first signal indicating that the door is closed is generated.

In one embodiment, the proximity sensor comprises a signal source configured to generate a first signal, an inductive interface coupled to the signal source, wherein the inductive interface is configured to inductively transmit the first signal and receive a second signal and add the first signal to the second signal to create a combined signal, a filter coupled to the inductive interface and configured to filter the first signal from the combined signal, and a decoding component configured to decode the second signal to read encoded data. In one embodiment, the encoded data is encoded via Manchester encoding and the encoded data comprises an identifier.

In one embodiment, a lock audit system comprises a locking mechanism configured to secure a door to a frame in a closed position when the door is in the closed position and the lock is engaged, a lock sensor coupled to the locking mechanism that generates a locking signal that indicates if the locking mechanism is engaged, a first component mounted on the door, and a second component mounted on the frame, wherein the first component and the second communicate when the first component and the second component are positioned in a first orientation relative to each other with the door in the closed position, and wherein the second component generates a closed signal indicating if the first component and second component are communicating, and a controller coupled to the lock sensor and the second component, wherein the controller receives the lock signal and the closed signal and determines if the door is lock and closed based on the lock signal and the closed signal.

By combining the electronic proximity sensor to the mechanical locking mechanism, mechanical locking can be confirmed. Further, exchanging an identifier ensures that only the door associated with the frame of the box or cabinet is engaged Furthermore, the audit system generates a record that tracks when the lock was engaged or disengaged and when the door was opened or closed. This record may be reviewed to determine when the cabinet was unlocked, how long it was unlocked, and by whom it was unlocked, thereby helping to monitor any access of the contents of the cabinet. These and other objects and advantages of the present invention will become more apparent from the following description taken in conjunction with the accompanying drawings.

DETAILED DESCRIPTION OF THE PREFERRED EMBODIMENT

Figure 1:
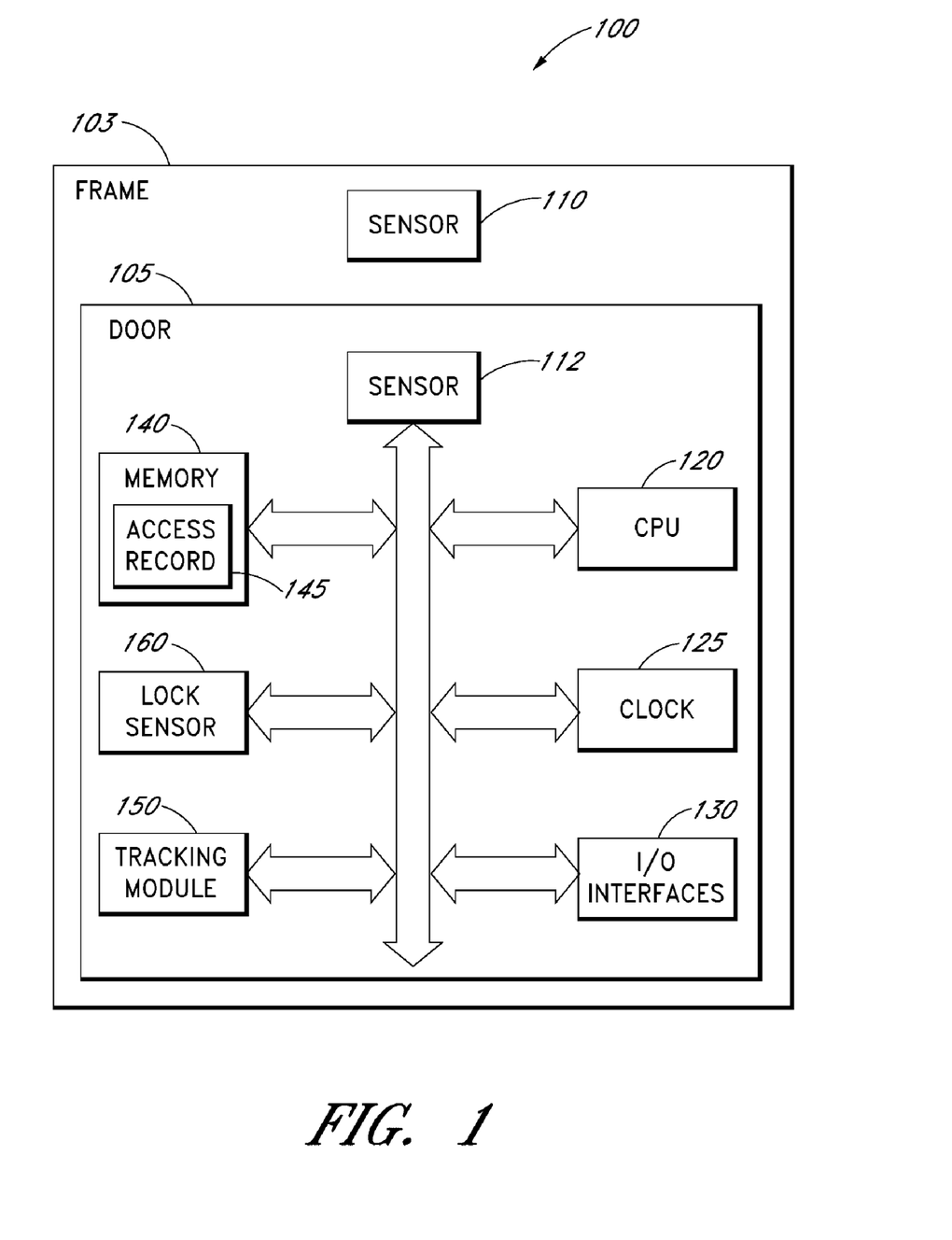
FIG. 1 is a block diagram illustrating one embodiment of a secure cabinet for holding pharmaceutical products.

Reference will now be made to the drawings wherein like numerals refer to like parts throughout. FIG. 1 is a block diagram illustrating one embodiment of a secure box or cabinet 100 for holding items such as pharmaceutical products. The cabinet 100 includes a frame 103 that creates a storage space, for example for storing pharmaceutical products. The cabinet 100 also includes a door 105 mounted to the frame 103. The door 105 may be opened to allow access to the contents of the frame 103 or closed to restrict access to the contents of the frame 103. The frame 103 and/or door 105 may be made of materials that are durable enough to resist an attempt to physically breach the cabinet 100, and in one embodiment are made of a metal, such as, for example, steel. The door 103 and frame 105 also include a locking mechanism to secure the door 103 in the closed position to prevent access to the contents of the cabinet 100. The locking mechanism may be any suitable lock and may be operated by any suitable interface, for example, mechanical key, mechanical combination, biometric data, electronic key, and keypad.

In FIG. 1, the cabinet 100 also includes a lock verification system. The lock verification system comprises a first sensor 110 that is mounted on the frame 103 and a second sensor 112 that is mounted on the door 105. The sensors 110, 112 may be configured to engage in electromagnetic communication with one another. In one embodiment, the first sensor 110 is passive and needs to be positioned in a predefined orientation relative to the second sensor 112 in order to be activated by the second sensor 112, which is active. Alternatively, the second sensor 112 may be passive and the first sensor 110 active, or both sensors 110, 112 may be active. Orientation may include, for example, distance, angle, and alignment. In one embodiment, the predetermined orientation requires the sensors to be brought into very close proximity to one another. The second sensor 112 may send a signal to the first sensor 110 to activate the first sensor, and the first sensor 110 may reply with a signal to the second sensor 112.

One or both of the first sensor 110 and the second sensor 112 may additionally transmit, encode, and/or verify a unique identifier associated with each cabinet 100. For example, both of the sensors 110, 112 may store an identification number that uniquely corresponds to the associated cabinet 100. When the sensors 110, 112 are in communication, the second sensor 112 may compare an identification number provided by the first sensor 110 to the identification number stored in the second sensor 112 to determine if they match. Alternatively, a controller, for example a central processing unit ("CPU") 120, may perform the comparison. If identification numbers match one or both of the sensors 110 112 may output a signal indicating whether or not the sensors 110, 112 are communicatively coupled with one another. The sensors 110, 112 may also output a signal indicating if there has been a change in the status of the communication between the sensors 110, 112.

The embodiment in FIG. 1 also comprises a lock sensor 160. The lock sensor 160 detects the actuation state of the lock and generates a signal that indicates if the lock is actuated and/or if the lock is not actuated. For example, if the lock comprises bolts that are extended when the lock is actuated, the lock sensor 160 detects when the bolts are extended and may generate a signal indicating the extension of the bolts. Also, the lock sensor 160 may generate a signal that indicates that the bolts are not extended.

In the embodiment shown in FIG. 1, the door 105 includes a CPU 120, which may include one or more microprocessor, and a clock 125. The door 105 also includes I/O devices and interfaces 130. The I/O devices and interfaces 130 may allow other computing devices to communicate with the cabinet 100 through a wired or wireless link, for example to retrieve data, modify software executable software, or upload data, and may include commonly available interfaces (e.g., USB, Firewire, SCSI, etc.) or a proprietary interface. Also, the I/O devices and interfaces 130 may allow a user to directly communicate with the cabinet 100. Such interfaces include by way of example keypads, screens, speakers, card readers, and biometric data readers. The cabinet 100 may be configured to permit communication between the locking mechanism and the I/O devices and interfaces 130 in order to require a user to provide an identifier, for example an identification code (e.g. a PIN number) or magnetic identification card, provide biometric data, and/or provide pharmaceutical information, for example the type and/or quantity of the pharmaceutical being removed from the cabinet, in order to disengage the locking mechanism.

Also in embodiment shown in FIG. 1, the cabinet 100 includes a memory 140. The memory 140 may include a random access memory ("RAM"), a flash memory, and/or a hard drive. The memory 140 includes an access record 145. The access record 145 may contain a log of some or all of the instances when the door 105 was secured or unsecured, which may include the instances when the sensors 110, 112 are brought into communication with one another or moved out of communication with one another and the instances when the locking mechanism is actuated or de-actuated, as well as the times of the instances. The log may be a time log indicating the date and time the cabinet 100 was secured or unsecured. The memory 140 may also include additional data, for example data related to control of the inventory of the cabinet 100. The additional data may include data regarding the contents of the cabinet 100, such as type of and quantity of pharmaceuticals added to the cabinet, the identification of the user who unlocked the cabinet at a particular time, a log of the person responsible for the cabinet at a given time (e.g., doctor, nurse, ambulance driver, emergency medical technician), and the type and quantity of pharmaceutical that the authorized person indicated was being removed during an access of the contents of the cabinet.

In the embodiment of FIG. 1, the cabinet 100 includes a tracking module 150. In general, the term "module," as used herein, refers to logic embodied in hardware, formware, and/or software, such as software instructions. The tracking module 150 may be executed by the CPU 120 to determine if the sensors 110, 112 are in communication with one another, determine if there has been a change in the communication between the sensors 110, 112, determine if the lock is actuated or not, and/or determine if there is a change in the state of the actuation of the lock. For example, the tracking module 150 may receive a signal from one or both of the sensors 110, 112 indicating a change in the communication between the sensors, and/or the tracking module 150 may intermittently or periodically poll the sensors 110, 112. The tracking module 150 may also receive the signal generated by the lock sensor 160, for example by polling the lock sensor 160. Also, the tracking module may access the clock 125 to determine the time it received any signal or performed any polling. The tracking module 145 may determine that the door 103 is secured only when the sensors 110, 112 are in the predetermined orientation and in communication via an encoded signal and the lock sensor 160 indicates that the lock is actuated. The tracking module 145 may store any of this information in the access record 145.

Figure 2:
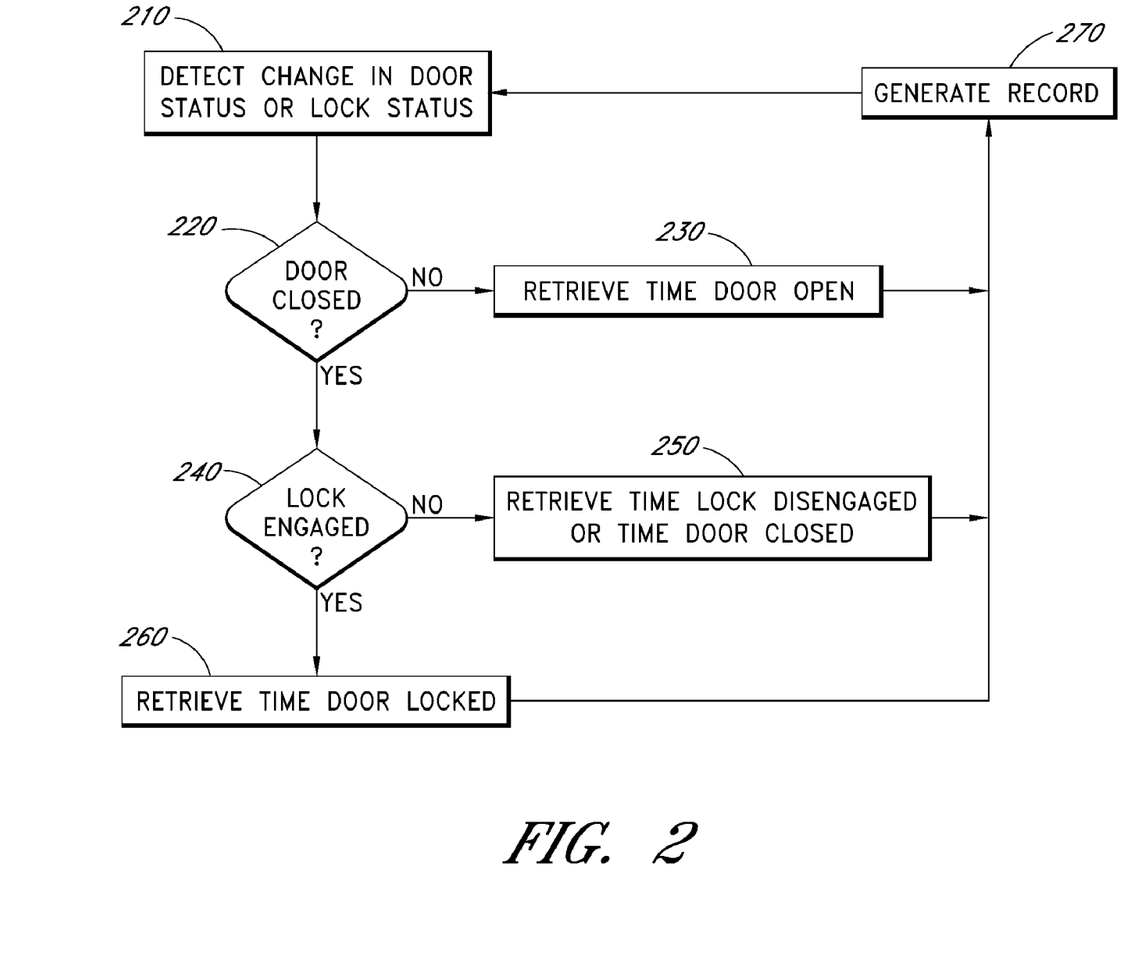
FIG. 2 is a flowchart illustrating one embodiment of a method of generating an access record.

FIG. 2 is a flowchart illustrating one exemplary embodiment of a method of generating an access record. Depending on the embodiment, the method of FIG. 2 may include additional or fewer blocks and the blocks may be performed in a different order than is illustrated. In block 210, a change is detected in the status of a door or the status of a lock. For example, a lock may transition from locked to unlocked or vice versa or a door may transition from open to closed or vice versa. If a change in the status of the door or lock is detected, the method proceeds to block 220.

In block 220, a determination is made if the state of She door has changed between open and closed. Sensors 110, 112 may be used to detect the change and/or determine if the door is open or closed. If in block 220 the door has changed to opened, the method proceeds to block 230 where the time that the door was opened is retrieved, and the method then proceeds to block 270. If in block 220 the state of the door is closed the method proceeds to block 240.

In block 240 a determination is made if the lock is engaged. This determination may be based at least in part on the signal from the lock sensor. If the lock is not engaged, the method proceeds to block 250. In block 250, a determination is made if the lock was previously engaged or if the door was previously open. If the lock was previously engaged, the time the lock was disengaged is retrieved. If the door was previously open, the time the door was closed is retrieved and the method proceeds to block 270. In block 260, the time that the door was locked is retrieved, and the method proceeds to block 270. It will be appreciated that the system may generate the record of the door being closed prior to determining whether the lock is engaged in state 240.

In block 270 a record is generated indicating the change in the status of the door or lock and the time of the change, for example by generating or adding information to the access record 145. In one embodiment, the record indicates only if the door is secure or unsecure, for example when both the door is closed and the lock is engaged, though in other embodiments the record may indicate the individual statuses of the lock and the door. If the record only indicated that the door was secured or unsecured, after retrieving the time that the door was locked in block 260, the block 270 a record would be generated indicating that the door was secured as the of time retrieved in block 260, and after retrieving the time in blocks 250 or 230 a record would be generated indicating that the door was unsecured as of the time retrieved in block 250 or 230.

This record may later be retrieved and used to determine the times that the door 105 was secured or unsecured and opened or closed and/or the times that the lock was engaged or disengaged. This record advantageously allows the later auditing of the accesses of the contents of the cabinet 100, such as to determine who accessed the contents of the cabinet and what was removed from the cabinet.

Figure 3:
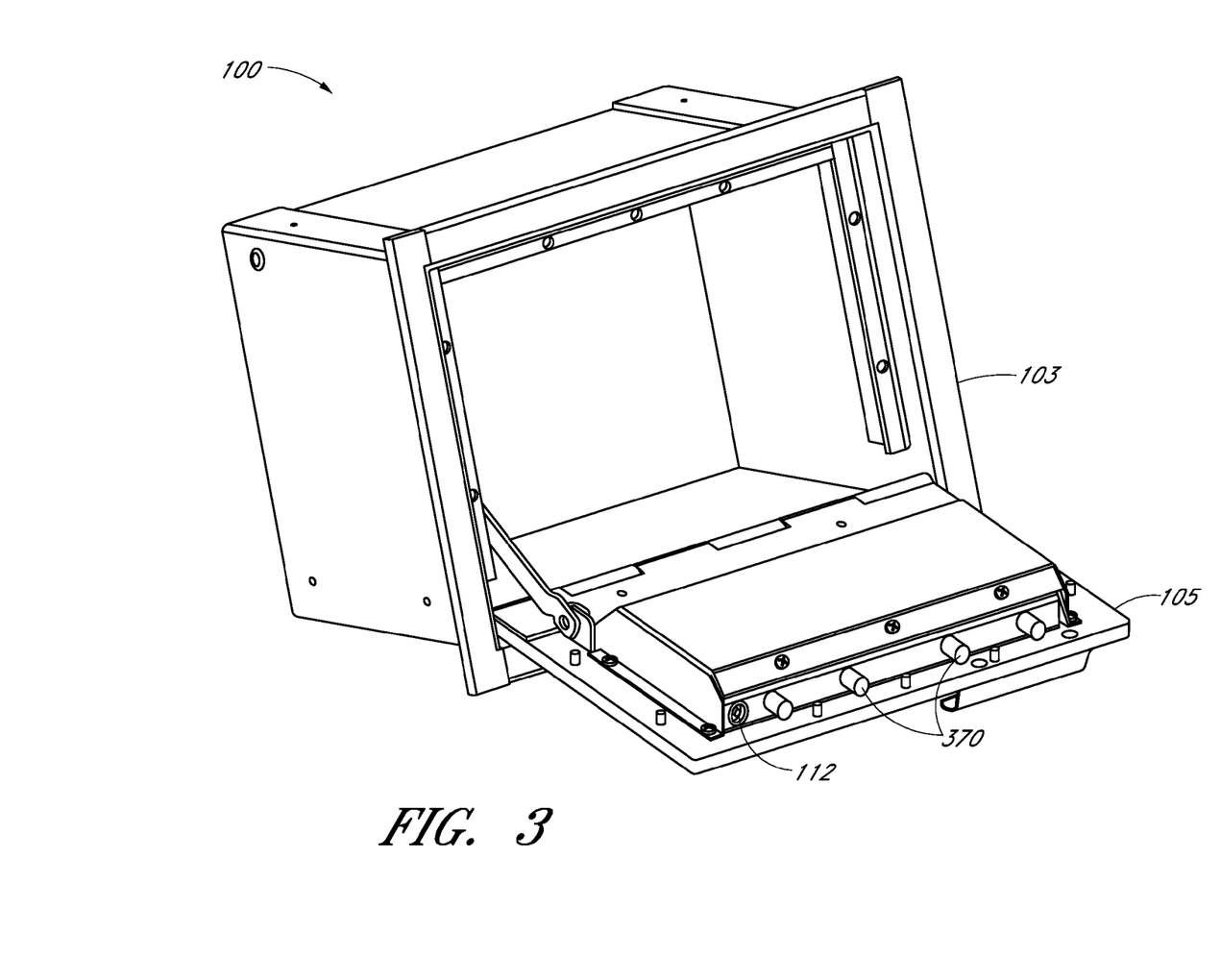
FIG. 3 is a perspective view of one embodiment of a sensor within the door of the cabinet.

FIG. 3 is a perspective view of one embodiment of a sensor 112 within the door 105 of the cabinet 100. The space 107 created by the frame 103 is also illustrated in FIG. 3. The door 105 includes one or more engaging member 370, which may comprise a bolt, for example.

Figure 4:
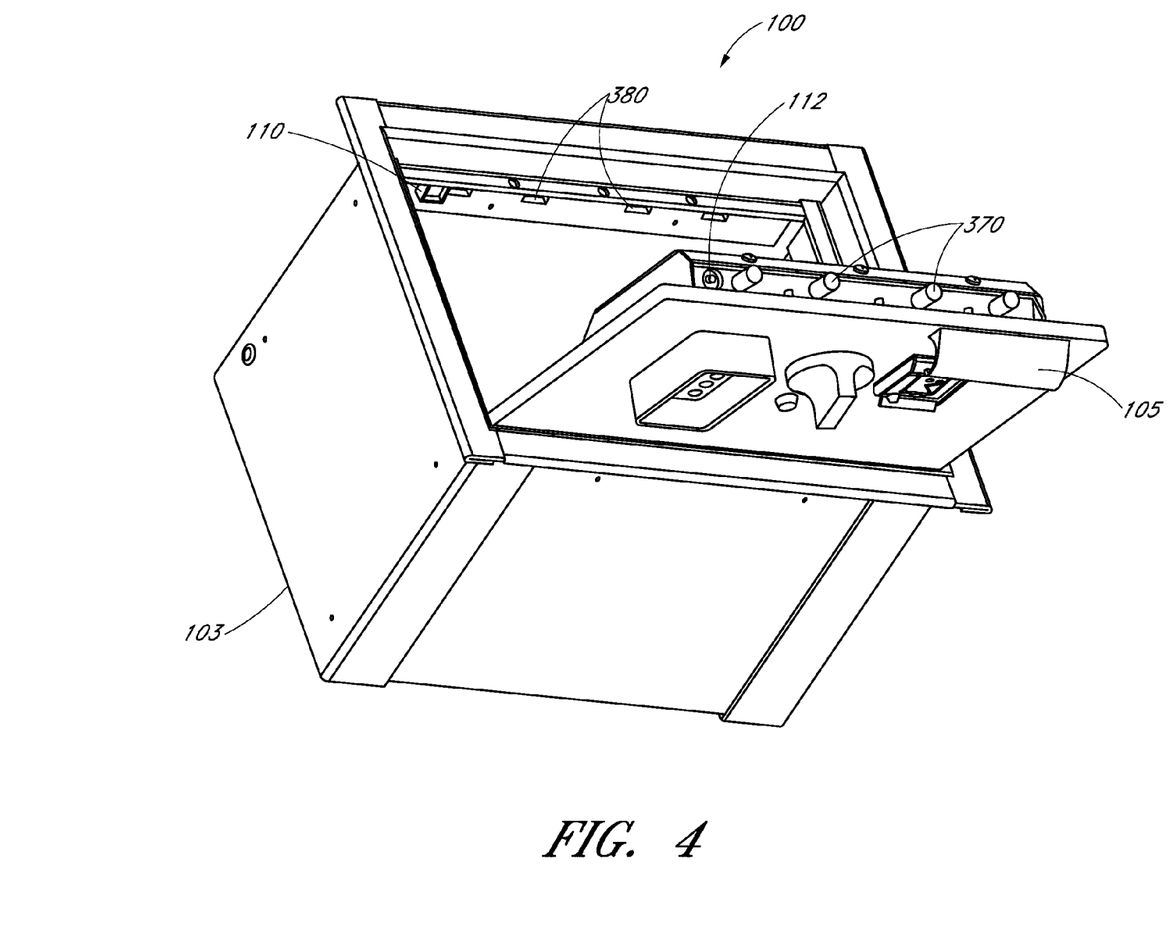
FIG. 4 is a perspective view of one embodiment of the sensor within the frame of the cabinet.

FIG. 4 is a perspective view of one embodiment of the sensor 110 within the frame 103 of the cabinet 100, positioned to correspond to the sensor 112 shown in FIG. 3. The sensors 110, 112 may be positioned differently in other embodiments. The frame 103 includes one or more receptacles 380 that correspond to the engaging members 370 and that are configured to receive the engaging members 370. When the door 105 is in the closed position relative to the frame 103 and the lock is engaged, the engaging members 370 are positioned within the corresponding receptacles 380, thereby securing the door 105 in the locked position. The predetermined orientation of the sensors 110, 112 corresponds to the position wherein the engaging members 370 may be actuated and engage the receptacles 380.

Figure 5A:
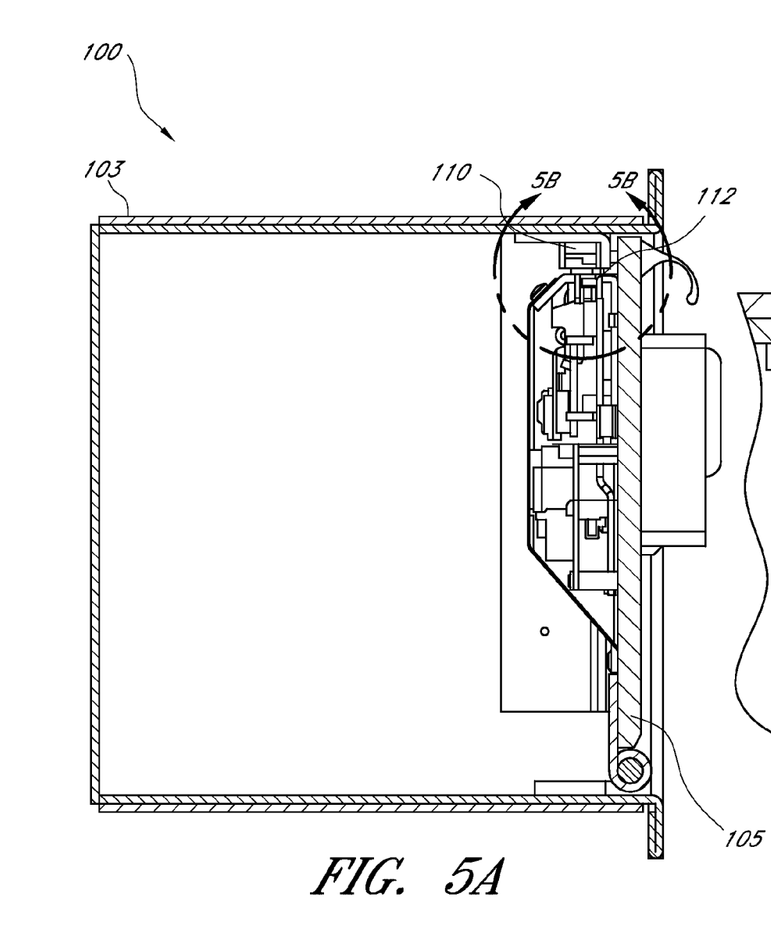
FIGS. 5A and 5B are a view of one embodiment of the positions of the door sensor and the frame sensor while the cabinet is closed.
Figure 5B:
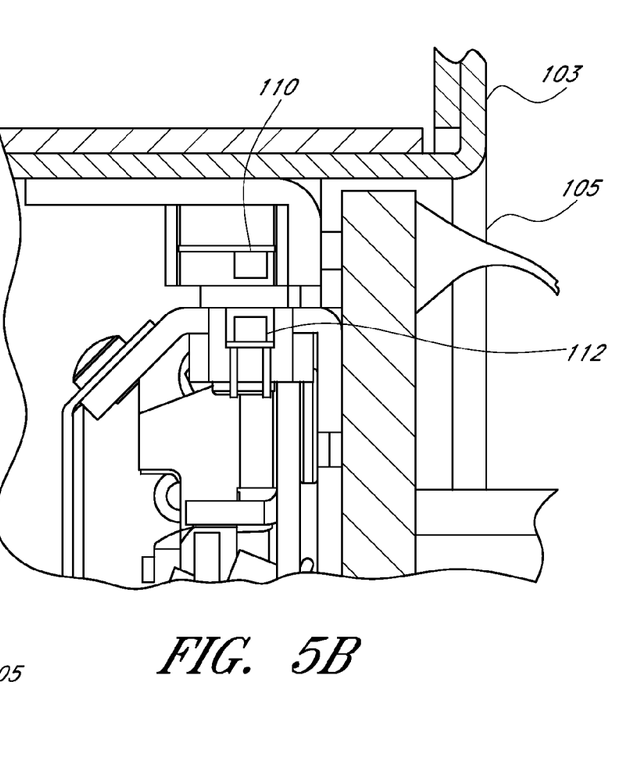

FIGS. 5A and 5B are a view of one embodiment of the positions of the door sensor 112 and the frame sensor 110 while the cabinet is closed. Once the door 105 is in the closed position, the sensors 110, 112 are within the predetermined orientation, for example within the predetermined proximity and alignment, and they communicate with one another. The sensors 110, 112 are mounted on the frame 103 and the door 105 of the cabinet 100 in such a way that they are only moved into the predetermined orientation when the door 105 is in the closed position.

Figure 6:
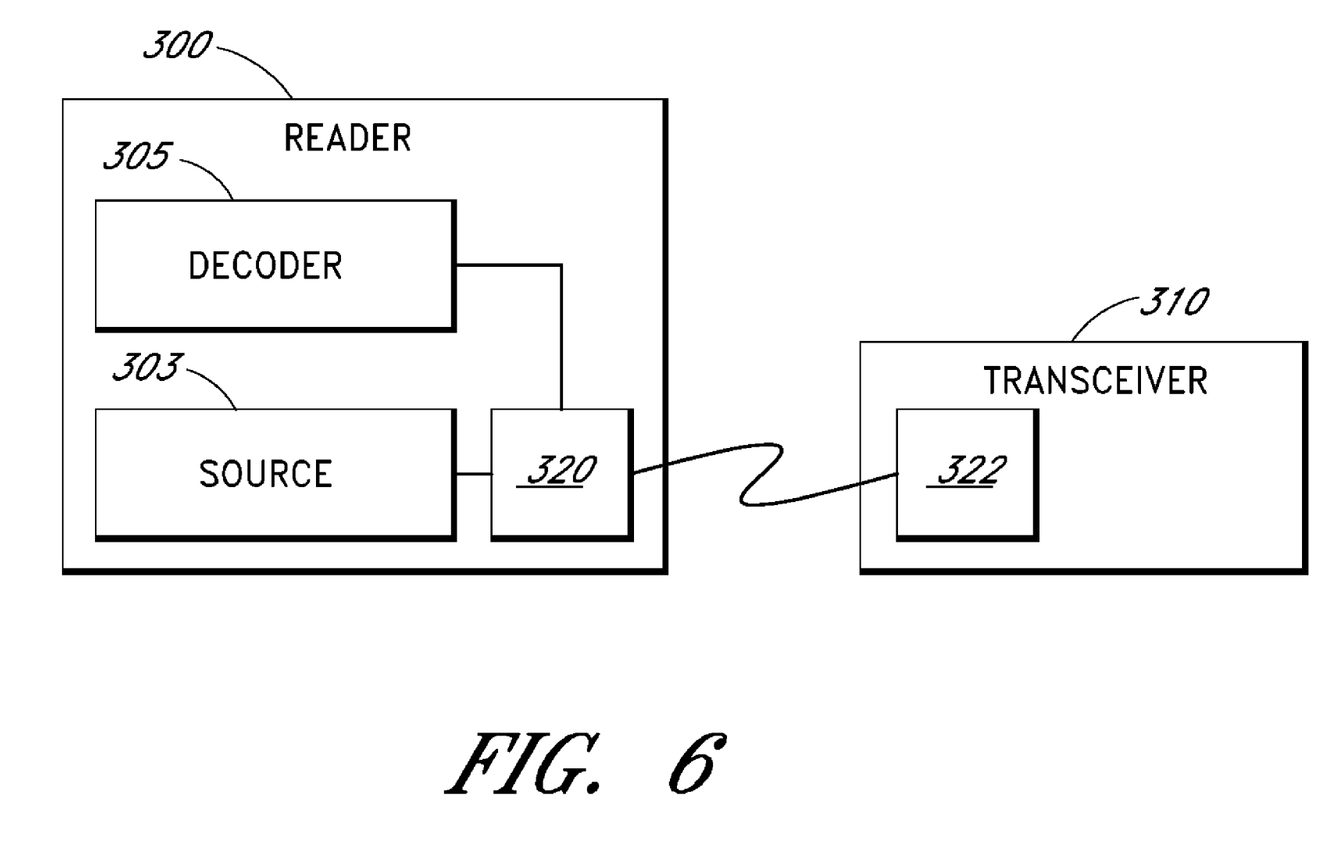
FIG. 6 is a block diagram of one embodiment of the sensors of the cabinet.

FIG. 6 is a block diagram illustrating one embodiment of the sensors of the cabinet. The sensors include a reader 300 and a transceiver 310. The reader 300 may be the sensor 110 mounted on the frame 103 or the sensor 112 mounted on the door 105, as shown in FIG. 1. Also, the transceiver 310 may be the sensor 110 mounted opposite to the reader 300, and thus may be on the frame 103 or on the door 105 depending on the placement of the reader 300. The reader 300 comprises a source 303 and a decoder 305. The source 303 receives an input voltage and generates an inductive source signal at the reader inductive interface 320. The signal has a peak-to-peak voltage large enough to allow the reader 300 and the transceiver 310 to communicate even when surrounded by metal, and is in the 200-300 Volts range in one embodiment. It will be appreciated that a metal cabinet 100 will absorb some of the source signal, and the source signal must therefore be strong enough to permit the reader 300 and the transceiver 310 to communicate even with a loss of part of the source signal. In one embodiment the source signal has an amplitude modulation frequency of about 125 KHz, though the source signal may be different frequencies in other embodiments.

The reader inductive interface 320 and the transceiver inductive interface 322 each comprise one or more inductors. When the reader inductive interface 320 communicates with the transceiver inductive interface 322, for example when they are in a predetermined orientation, induction conveys the source signal to the transceiver inductive interface 322. In one embodiment, the transceiver inductive interface 322 and the reader inductive interface 320 are substantially identically sized, and the interfaces 320, 322 may communicate when they are about 130 mils apart along the Z axis and are approximately aligned along the X and Y axes. In other embodiments, the interfaces 320, 322 may communicate if they are within 5-10 mils of being aligned along the X and Y axes, though in other embodiments the interfaces 320, 322 may communicate if they are within about +25 mils of being aligned along the X and Y axes. Also, the interfaces 320, 322 may communicate if they are within about 0 to 200 mils of each other along the Z axis. When mounted in a metal cabinet 100, if the reader 300 and the transceiver 310 are not properly aligned then the metal of the cabinet may absorb most or all of the source signal, thereby preventing communication. Thus, the reader 300 and the transceiver 310 provide a range in which communication is permitted, which allows communication even if the door and frame shift slightly during use, but also create a tolerance small enough that the door and frame must actually be closed in order for the reader 300 and the transceiver 310 to communicate.

The transceiver inductive interface 322 receives the source signal from the reader inductive interface 320. The transceiver 310 may also comprise a voltage regulator that may receive the source signal and covert it to a lower voltage signal. In one embodiment, the lower voltage signal is about 5 Volts, though it may be different in other embodiments. The source signal and/or the lower voltage signal may be used to power parts of or all of the transceiver 310. For example, the lower voltage signal may be used to power a processor in the transceiver 310. Also, the transceiver 310 may be powered only when receiving the source signal, so the reader inductive interface 320 may need to transmit the source signal as long as it is desired to keep the transceiver 310 powered. Powering the transceiver 310 through the source signal advantageously eliminates the need to connect a power supply to the transceiver, such as by connecting a wire to it, which may require modifications of the cabinet 100.

When the transceiver 310 is powered, it generates a transceiver signal on the transceiver inductive interface 322, which is transmitted to the reader inductive interface 320. In one embodiment, the transceiver signal generates an interference pattern on the source signal on the reader inductive interface 320. Differences in the amplitude modulation frequency of the source signal and the transceiver signal facilitate the separation of the signals. In one embodiment, the transceiver signal has an amplitude modulation frequency of 1000 Hz. Thus, if the source signal is 125 KHz, the transceiver signal would be a 1000 Hz interference pattern on the 125 KHz signal. In another embodiment, the transceiver signal has an amplitude modulation frequency of up to 1/10 of the source signal modulation frequency.

The transceiver signal may include an encoded binary signal, which may be generated by the processor in the transceiver. In one embodiment, the transceiver signal is encoded using a code in which each data bit is indicated by at least one transition between a 1 and a 0, such as Manchester encoding. The transition that carries data may be in the middle of each bit period, though the transition signal may have a transition at the start of each bit period that does not carry data. This allows the signal to be self clocking and eliminate D.C. bias. The clock rate of the encoded signal may be identical to the frequency of the transceiver signal, for example, 1000 Hz. Thus, if one data bit is carried in each clock cycle, a 1000 Hz signal would correspond to an encoded signal that transmits 1000 bits per second. The encoded signal may be used to transmit an identifier. In one embodiment, the identifier is a 32 bit number, though the identifier may be other bit lengths. A matching identifier may be stored in the reader 300. The identifiers may be unique to the reader 300 and the transceiver 310 and may be hardwired into one or both of the transceiver 310 and the reader 300 at the time of their manufacture.

Upon receiving the transceiver signal, the reader inductive interface 320 carries both the source signal and the transceiver signal. The source signal and transceiver signal are both provided to the decoder 305 of the reader 300. When the transceiver signal is an interference patter on the source signal at the reader inductive interface 320, both of the signals may be provided to the decoder 305 by providing the source signal from the reader inductive interface 320 to the decoder 305. The decoder 305 filters the source signal, leaving the transceiver signal. For example, when the source signal is 125 KHz and the transceiver signal is 1000 Hz, the decoder may use a low-pass filter to filter the source signal.

The transceiver signal may then be amplified by the decoder 305 to clean the edges in the transitions of the signal in order to help delineate between a high and a low state in the transceiver signal in order to extract binary data from the transceiver signal. The decoder 305 may also comprise a processor that decodes the encoded transceiver signal, extracts an identifier from it, and analyzes the extracted identifier to determine if the transceiver 310 corresponds to the reader 300, for example when the identifier received from the transceiver 310 is identical to an identifier stored in the reader 300. If the transceiver 310 corresponds to the reader 300, the reader 300 then generates a signal indicating that the door is closed. The use of identifiers advantageously prevents the reader 300 from being fooled through the use of another sensor, e.g., another transceiver 310 that does not belong to the cabinet 100 or by bringing a metal object close to the reader 300.

Thus, the voltage level of the signals, the limited range of communication of the sensors, the encoding, the use of identifiers, and the mounting of the sensors on the cabinet such that they can only be brought into the predetermined orientation when the door is closed allow the sensors to determine when the door and frame of a metal cabinet 100 are actually secured and resist deception. Thus, the cabinet 100 facilitates the control of its contents by generating a record of the times that the cabinet was secured or unsecured and the record that is generated is reliable because the sensors are very difficult to thwart.

While certain embodiments of the invention have been described, these embodiments have been presented by way of example only, and are not intended to limit the scope of the present invention. Indeed, novel methods and systems described herein may be embodied in a variety of other forms. Furthermore, various omissions, substitutions and changes in the form of the methods and system described herein may be made without departing form the spirit of the present invention.

What is claimed is:

1. A storage container for medical pharmaceuticals, the container comprising:

a frame that defines a partially enclosed space that is configured to receive medical pharmaceuticals, wherein the frame defines an opening;

a door mounted to the frame so as to be movable between an open position, whereby access to the medical pharmaceuticals can be obtained, and a closed position whereby the medical pharmaceuticals can be secured within the partially enclosed space;

a locking mechanism that secures the door to the frame in the closed position; and a lock verification system that includes a first component mounted on the door and a second component mounted on the frame, wherein the first component and the second component are inductively coupled so that when the first component and the second component are positioned in a first orientation relative to each other with the door in the closed position a first signal indicating that the door is closed is generated and wherein the second component transmits a first identifier to the first component when the first component and the second component are positioned in the first orientation, the first component compares the first identifier to a second identifier and generates the first signal if the first identifier corresponds to the second identifier.

2. The container of claim 1, wherein the door and frame comprise metal.

3. The container of claim 1, wherein at least one of the first and second components generates a second signal indicative of when the components have been moved from the first orientation thereby indicating that the door has been opened.

4. The container of claim 3, further comprising a controller that receives the first signal, wherein the controller determines if the door was opened or closed based on at least the first signal and generates a record indicating the time the door was opened or closed in order to facilitate inventory control of the medical pharmaceuticals.

5. The container of claim 4, further comprising a sensor coupled to the locking mechanism, wherein the sensor generates a third signal indicating if the locking mechanism is engaged, and wherein the controller determines if the locking mechanism is engaged or disengaged based on the third signal and generates a record indicating the time the locking mechanism was engaged or disengaged.

6. The container of claim 5, wherein
the controller determines if the door is secure based on at least the first and third signals; and
the controller generates a record indicating the time during which the door was secure.

7. The container of claim 6, wherein the first identifier and the second identifier both comprise 32 bits and the first identifier is encoded when transmitted by the second component.

8. A storage container comprising:
a frame that defines a partially enclosed space that is configured to receive medical pharmaceuticals, wherein the frame defines an opening;
a door mounted to the frame so as to be selectively movable between an open position and a closed position; and
a first sensor mounted on the door and a second sensor mounted on the frame, wherein the first sensor comprises
a first signal source configured to generate a first signal;
a first interface coupled to the signal source, wherein the first interface is configured to inductively transmit the first signal and receive a second signal when positioned in a first orientation relative to the second sensor; and wherein the second sensor comprises
a second signal source configured to generate a second signal;
a second interface coupled to the second signal source, wherein the second interface is configured to receive the first signal and inductively transmit the second signal when positioned in the first orientation and wherein the first sensor is further configured to add the first signal to the second signal to create a combined signal, and wherein the first sensor further comprises a filter that receives the combined signal and removes the first signal from the combined signal.

9. The storage container of claim 8, wherein the first signal powers the second sensor.

10. The storage container of claim 8, wherein the first interface receives the second signal as an interference pattern on the first signal.

11. The storage container of claim 10, wherein the second sensor further comprises an encoding component configured to encode binary data into the second signal, wherein the binary data is indicated by a transition between a low state and a high state in a center of a bit period.

12. The storage container of claim 11, wherein the first sensor further comprises a decoding component that extracts encoded binary data from the second signal.

13. The storage container of claim 8, wherein the first signal is about 200 to 300 volts peak-to-peak.

14. The storage container of claim 8, wherein the first signal has an amplitude modulation frequency of about 125 KHz and the second signal has an amplitude modulation frequency of about 1000 Hz.

15. The storage container of claim 8, wherein the first and second sensors are in the first orientation if they are positioned within about 25 mils of being aligned along the X and Y axes.

16. The storage container of claim 8, wherein the first and second sensors are in the first orientation if they are positioned within about 200 mils of each other along the Z axis.

17. A lock audit system comprising:
a locking mechanism configured to lock a door to a frame in a closed position when the door is in the closed position and the locking mechanism is engaged;
a lock sensor coupled to the locking mechanism and configured to generate a locking signal that indicates if the locking mechanism is engaged;
means for detecting if the door and the frame are in the closed position;
means for generating a second closed signal if the door and frame are in the closed position;
a controller configured to receive the lock signal and the closed signal and determine if the door is locked and closed based on the lock signal and the closed signal, and wherein the controller generates a record of the times that the door is locked and the times that the door is closed wherein the controller receives the closed signal as an interference pattern of the lock signal.

18. The lock audit system of claim 17, further comprising a lock interface that controls the engagement of the lock mechanism, wherein the lock interface requires a user to provide a user identifier to disengage the locking mechanism, and wherein the controller adds the user identifier and the time the user identifier was provided to the record.

* * * * *